US005919697A

United States Patent [19]

Salmon et al.

[11] Patent Number: 5,919,697

[45] Date of Patent: Jul. 6, 1999

[54] COLOR CLARIFICATION METHODS

[75] Inventors: Sonja I. Salmon; Anita R. Mishra, both of Raleigh, N.C.; Jack B. Nielsen, Hellerup, Denmark

[73] Assignees: Novo Nordisk A/S, Bagsvaerd, Denmark; Novo Nordisk Biochem North America, Inc., Franklinton, N.C.

[21] Appl. No.: 08/733,481

[22] Filed: Oct. 18, 1996

[51] Int. Cl.[6] .......................... D06M 16/00; C12Q 1/00; C12N 9/00; C07K 13/00

[52] U.S. Cl. .......................... 435/263; 435/4; 435/183; 435/263; 510/367; 510/302; 510/276; 510/515; 536/123.1; 530/350; 252/86; 252/87; 252/875; 252/174

[58] Field of Search .......................... 510/367, 302, 510/276, 515; 585/455; 435/4, 183, 263; 536/123.1; 530/350; 525/50; 252/86, 87, 875, 174

[56] References Cited

U.S. PATENT DOCUMENTS

| | | | |
|---|---|---|---|
| H1513 | 1/1996 | Murch et al. . | |
| 4,746,456 | 5/1988 | Kud et al. . | |
| 4,846,994 | 7/1989 | Kud et al. | 254/174.21 |
| 5,352,389 | 10/1994 | Gazzani | 252/544 |
| 5,445,747 | 8/1995 | Kvietok et al. | 252/86 |
| 5,560,748 | 10/1996 | Surutzidis | 8/111 |

FOREIGN PATENT DOCUMENTS

| | | |
|---|---|---|
| 0 381 431 | 8/1990 | European Pat. Off. . |
| 0 454 126 A1 | 10/1991 | European Pat. Off. . |
| 0 612 842 A2 | 8/1994 | European Pat. Off. . |
| 43 44 490 A1 | 6/1995 | Germany . |
| WO 91/19794 | 12/1991 | WIPO . |
| WO 91/19807 | 12/1991 | WIPO . |
| WO 93/21294 | 10/1993 | WIPO . |
| WO 95/02675 | 1/1995 | WIPO . |
| WO 95/33028 | 12/1995 | WIPO . |
| WO 95/35363 | 12/1995 | WIPO . |
| WO 96/20997 | 7/1996 | WIPO . |

*Primary Examiner*—Scott W. Houtteman
*Attorney, Agent, or Firm*—Steve T. Zelson, Esq; Cheryl H. Agris, Esq

[57] ABSTRACT

The invention is directed to agents used in the retention of color values on fabrics formed from cellulose fibers (color clarification agents) and to a method for treatment of such fabrics. The method comprises treating a colored fabric with a cellulase and a polymer selected from the group consisting of a polyalkylene oxide graft polymer, a polyamino acid polymer, and a carboxylated polysaccharide polymer in an amount effective to preserve the color of the fabric after at least one wash cycle.

20 Claims, 1 Drawing Sheet

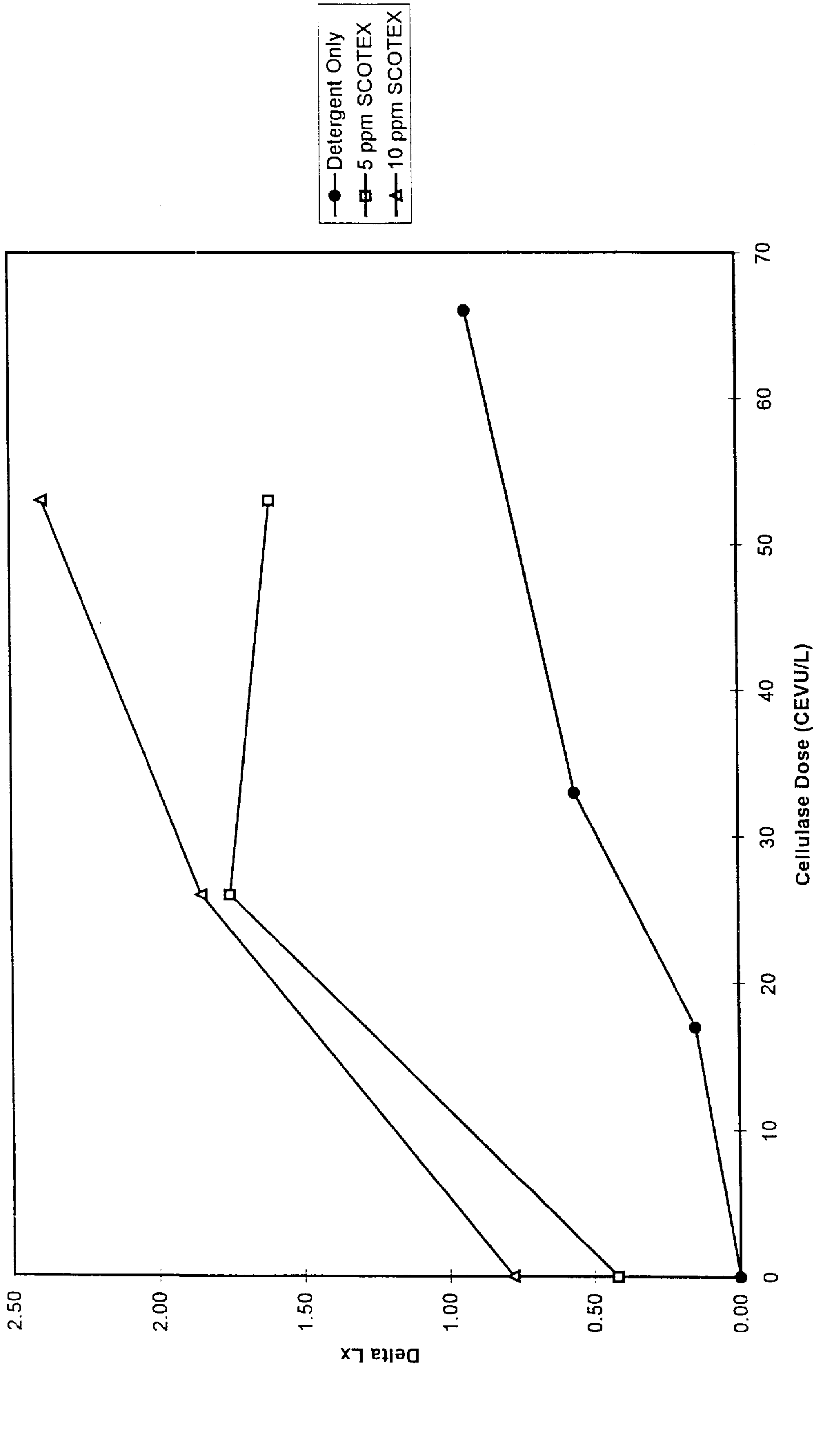
Figure 1. Delta Lx versus Cellulase Dose

COLOR CLARIFICATION METHODS

1. FIELD OF THE INVENTION

The invention is directed to agents used in the retention of color values on fabrics formed from cellulose fibers (color clarification agents) and to a method for treatment of such fabrics.

2. BACKGROUND OF THE INVENTION

Clothes made from cellulose fabrics often develop a grayish cast or appearance with wear and repeated washing. This unwanted effect is particularly evident in garments dyed with dark colors. It is believed that the grayish cast is caused, at least in part by generation of disordered fibers through mechanical action. The mechanical action incident to washing tears, splits, and/or breaks fibers, generating superficial disorder at the surface of the strands or threads from which the garment is made. Even after a thorough washing in which all ordinary dirt, e.g., protein, oil, starch and dust, has been removed, the clothes look faded and worn.

U.S. Pat. No. 4,738,682 disclosed a color clarification method involving the use of cellulase alone as a color clarification agent. As defined herein, a "color clarification agent" is an agent involved in the preservation or restoration of the initial appearance of a colored fabric throughout multiple washing cycles by removing fuzz and pills from the surface of the garment and/or fabric. Such an agent has, to some extent, improved the appearance of washed fabrics relative to washed fabrics not treated with the agent. Colored fabrics dyed with fugitive dyestuffs, such as those belonging to the direct dye class of dyes, develop a particularly faded appearance after repeated washing due to loss of dye from the fabric. The loss of color contributes to the aged look of the fabric. This color loss is not maintained or restored by treatment with cellulase alone. Therefore, a need exists for an improved agent which will more effectively restore the attractive look of fabrics which have developed a grayish cast after frequent washing, or maintain the original appearance of fabrics that are washed many times, thereby offering the consumer a chance to avoid discarding worn looking, but still serviceable cellulose fabric garments.

Some surfactants have been found to boost the action of cellulase. These include ethoxylated $C_{12}$–$C_{20}$ alcohols or alkyl-phenols with 10–100 ethoxy groups (WO 91/19794). Polymers of one or more monomers selected from the group of vinyl pyrrolidone, vinyl alcohol, vinyl carboxylate (especially polyvinyl acetate), acrylamide, soluble acrylates, and copolymers of these (WO 91/19807) are reported to increase cellulase enzymatic effect for color clarification of textiles. However, no other polymers are known in the art to have such boosting action.

Polymers, such as polyvinyl pyrrolidone, are known in the art to suspend particles in solution and sequester dyes in solution, thereby preventing dye transfer from one fabric to another (V. B. Croud, The influence of washing powder components on dye loss and dye fading, JSDC, 112 (1996) 117–122; F. Runge et al., Binding equilibria of multiazo dyes with polymeric dye transfer inhibitors, Berichte der Bunsen-Gesellschaft-Physical Chemistry Chemical Physics, 100, No. 5 (1996) 661–670). Other polymers reported to provide dye transfer inhibition are polyamine N-oxides (WO 95/33028) and combinations of polyamino acids and polyalkylene glycols (WO 95/16767) but these have not been reported to give improvement of cellulase color clarification performance.

3. SUMMARY OF THE INVENTION

The invention is directed to a color clarification method comprising treating a colored fabric with a cellulase and a polymer selected from the group consisting of a polyalkylene oxide graft polymer, a polyamino acid polymer, and a carboxylated polysaccharide polymer in an amount effective to preserve the color of the fabric after at least one wash cycle.

It has surprisingly been found that the addition of a polymer selected from the group consisting of a polyalkylene oxide graft polymer, a polyamino acid polymer, and a carboxylated polysaccharide polymer boosts the color clarification effect of a cellulase. Polyamino acids (EP 612842) and carboxylated polysaccharides (U.S. Pat. No. 3,723,322) are known in the art as detergent builders where they function as dispersants and to sequester metal cations and improve detergency and soil removal.

In the prior art, a polyalkylene oxide graft polymer has been found to inhibit grayness, i.e., the redeposition of soil particles and greases on the wash during washing (U.S. Pat. Nos. 4,846,994 and 4,746,456), in detergent compositions (U.S. Pat. No. 4,874,537, WO 95/22593), or as anticrease agents for dying, whitening, bleaching, or washing textiles (U.S. Pat. No. 4,705,525). Polymers of esterified polyalkylene glycol backbone grafted with ethyenically unsaturated monomers have also been used as dyeing assistants to give increased dye yield (U.S. Pat. No. 4,705,525).

Therefore, in one embodiment, a colored fabric is treated with cellulase and a polymer selected from the group consisting of a polyalkylene oxide graft polymer, a polyamino acid polymer, and a carboxylated polysaccharide polymer in an amount effective to preserve the color of said fabric relative to a fabric treated without polymer but with cellulase after at least one wash cycle.

It has also surprisingly been found that cellulase boosts the color clarification effect of polymers such as polyamino acids and carboxylated polysaccharides. Therefore, in another embodiment, the colored fabric is treated with cellulase and a polymer selected from the group consisting of a polyamino acid polymer and a carboxylated polysaccharide polymer in an amount effective to preserve the color of said fabric relative to a fabric treated without cellulase but with polymer after at least one wash cycle.

4. BRIEF DESCRIPTION OF THE FIGURES

FIG. 1 shows Celluzyme 2.0 L dosed in 2 g/L of a commercially available light duty liquid detergent (Soflan®, Colgate-Palmolive), with 0, 5, and 10 ppm SCOTEX XL after 9 Mini-Terg wash/dry cycles.

5. DETAILED DESCRIPTION OF THE INVENTION

5.1 Fabric

The method of the invention is directed to colored cellulose fabrics, i.e., fabrics with another color than white. The effect is most striking on fabrics of dark colors, particularly those colored with fugitive dyestuffs, such as belong to the direct dye class of dyestuffs.

5.2. Cellulase

The cellulase to be used according to the present invention may be any cellulase having cellulolytic activity, i.e., hydrolyzes cellulose, either in the acid, the neutral or the alkaline pH-range and having cellobiohydrolase, exocellobiohydrolases, endoglucanases, and/or β-glucosidase activity (multicomponent or monocomponent). The cellulase may be of fungal or bacterial origin, which may be obtainable or isolated and purified from microorganisms which are known to be capable of producing cellulolytic enzymes, e.g., species of Humicola, Coprinus, Thielavia, Myceliopthora, Fusarium, Myceliophthora, Acremonium, Cephalosporium, Scytalidium, Penicillium or Aspergillus (see, for example, EP 458162), especially those produced or producible by a strain selected from the species *Humicola insolens* (reclassified as *Scytalidium thermophilum,* see for example, U.S. Pat. No. 4,435,307), *Coprinus cinereus, Fusarium oxysporum, Myceliophthora thermophila, Meripilus giganteus, Thielavia terrestris,* Acremonium sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum,* and *Acremonium furatum;* preferably from the species *Humicola insolens,* DSM 1800, *Fusarium oxysporum,* DSM 2672, *Myceliophthora thermophila,* CBS 117.65, Cephalosporium sp., RYM-202, Acremonium sp., CBS 478.94, Acremonium sp., CBS 265.95, *Acremonium persicinum,* CBS 169.65, *Acremonium acremonium,* AHU 9519, Cephalosporium sp., CBS 535.71, *Acremonium brachypenium,* CBS 866.73, *Acremonium dichromosporum,* CBS 683.73, *Acremonium obclavatum,* CBS 311.74, *Acremonium pinkertoniae,* CBS 157.70, *Acremonium roseogriseum,* CBS 134.56, *Acremonium incoloratum,* CBS 146.62, and *Acremonium furatum,* CBS 299.70H. Cellulase may also be obtainable from Trichoderma (particularly *T. viride, T. reesei,* and *T. koningii*), alkalophilic Bacillus (see, for example, U.S. Pat. No. 3,844, 890 and EP 458162), and Streptomyces (see, for example, EP 458162).

The cellulase used in the method of the present invention may be produced by fermentation of the above mentioned microbial strain on a nutrient medium containing suitable carbon and nitrogen sources and inorganic salts, using procedures known in the art (see, e.g., Bennett, J. W. and LaSure, L. (eds.), *More Gene Manipulations in Fungi,* Academic Press, Calif., 1991). Suitable media are available from commercial suppliers or may be prepared according to published compositions (e.g., in catalogues of the American Type Culture Collection). Temperature ranges and other conditions suitable for growth and cellulase production are known in the art (see, e.g., Bailey, J. E., and Ollis, D. F., Biochemical Engineering Fundamentals, McGraw-Hill Book Company, N.Y., 1986).

As defined herein, the term "fermentation" is any method of cultivation of a cell resulting in the expression or isolation of the cellulase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the cellulase to be expressed or isolated.

The resulting cellulase produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

Alternatively, the cellulase used in the method of the present invention may be a monocomponent, i.e., a component essentially free of other cellulase components usually occurring in a cellulase system produced by a given microorganism. The single component may be a recombinant component, i.e., produced by cloning of a DNA sequence encoding the single component and subsequent cell transformed with the DNA sequence and expressed in a host, cf. e.g. International Patent Applications WO 91/17243 and WO 91/17244 which are hereby incorporated by reference. Other examples of monocomponent cellulases include but are not limited to those disclosed in JP-07203960-A and WO-9206209. The host is preferably a heterologous host, but the host may under certain conditions also be the homologous host.

Cellulase hydrolyzes carboxymethyl cellulose (CMC), thereby decreasing the viscosity of the incubation mixture. The resulting reduction in viscosity may be determined by a vibration viscosimeter (e.g. MIVI 3000 from Sofraser, France). Determination of the cellulolytic activity, measured in terms of Cellulase Viscosity Unit (CEVU), may be determined according to the assay described below.

The CEVU assay quantifies the amount of catalytic activity present in the sample by measuring the ability of the sample to reduce the viscosity of a solution of carboxymethyl cellulose (CMC). The assay is carried out at 40° C.; pH 9.0; 0.1M phosphate buffer; time 30 min; CMC substrate (33.3 g/L carboxymethyl cellulose Hercules 7 LFD); enzyme concentration approx. 3.3–4.2 CEVU/ml. The CEVU activity is calculated relative to a declared enzyme standard, such as Celluzyme® Standard 17-1194 (obtained from Novo Nordisk A/S, Bagsvaerd, Denmark).

5.3. Polymers

The polymers used in the method of the present invention may be a polyethylene oxide graft polymer, a polyamino acid polymer or a carboxylated polysaccharide.

5.3.1. Polyalkylene Oxide Graft Polymer

The polyalkylene oxide graft polymers used in the method of the present invention are described and claimed in U.S. Pat. Nos. 4,846,994 and 4,746,456. These polymers may be obtainable by grafting a (a) polyalkylene oxide backbone having a molecular weight of about 300–100,000 with (b) vinyl acetate, vinyl propionate, vinyl esters of C2–C6 saturated monocarboxylic acids, methyl and ethyl acrylate, methyl and ethyl methacrylates, and their mixtures, in a weight ratio of (a) to (b) of about 1:0.2 to about 1:10. The ester groups may be partially hydrolyzed, e.g., to an extent of up to about 15%. In a preferred embodiment, the polyalkylene oxide has a molecular weight of from about 1000 to about 50,000, and the weight ratio of polyalkylene oxide to grafted monomer(s) (b), preferably vinyl acetate or vinyl propionate, is from about 1:0.5 to about 1:6.

The polyalkylene oxide may contain units of ethylene oxide propylene oxide, and/or butylene oxide. In a preferred embodiment, the polymer used is derived from ethylene oxide having a molecular weight of about 1,000–50,000. The grafted monomer is vinyl acetate or vinyl propionate, and the weight ratio of polyethylene oxide to grafted vinyl monomer is from about 1:0.5 to 1:6.

Alternatively, the polyalkylene oxide polymer may be obtained according to the methods disclosed in U.S. Pat. No. 4,705,525.

5.3.2. Polyamino acid Polymers

In a preferred embodiment of the invention, the polyamino acid is prepared from aspartic acid, glutamic acid or a combination thereof.

The polyaspartic acid and water soluble salts thereof useful in the present invention can be described by the following formula:

(I)

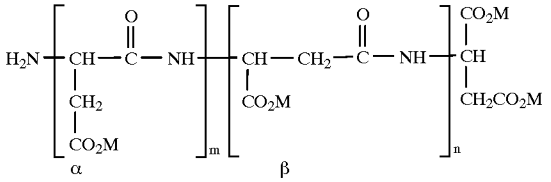

wherein m+n is from about 5 to about 85, preferably from about 16 to about 42, the ratio of α/β is from 1/0 to 0/1 (typically 1/4 to 4/1, in most cases about 1/3); and M is hydrogen or a neutralising cation such as alkali metal (e.g. sodium or potassium), ammonium or substituted ammonium (e.g. mono-, di-, or triethanolammonium). The α and β blocks in the above formula can vary in number of repeating units and can be randomly distributed along the chain. The absolute configuration about the asymmetric carbon atom can be D or L.

The molecular weight of the polyaspartates herein can be from about 600 to about 40000, and is preferably in the range of from about 1000 to about 10000, based on the acid form.

Polyaspartic acid can be prepared by known methods. Preparation by the reaction of maleic acid and ammonia is described in U.S. Pat. No. 4,438,461. Other methods are described e.g. in Sandek et al., Biopolymers, Vol.20, p.1615 (1981).

A method is described in U.S. Pat. No. 5,057,597, wherein an agitated fluid bed of freely flowing, solid particulate aspartic acid is formed, then heated to and maintained at 180° C. to 250° C. for a time sufficient to polymerize the acid and drive off the water, while at the same time maintaining a mean particle size of about 150 μm or less and providing a degree of agitation sufficient to maintain the particles in a substantially free-flowing state. The product of this heating process is the anhydropolyaspartic acid, which is then recovered from the fluidized bed and hydrolyzed to a polyaspartate salt with aqueous base (e.g. aqueous sodium hydroxide). This process typically produces polyaspartate salts having (on an acid basis) a molecular weight of from about 1600 to about 3600, i.e. m+n in the above formula is from about 13 to about 30. If desired, the hydrolysis of anhydropolyaspartic acid can be conducted in acid media to produce polyaspartic acid.

The polyglutamic acid and water soluble salts thereof can be described by the following formula:

(II)

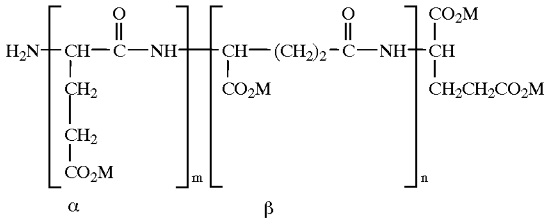

wherein m+n, the ratio of α/β, and M has the meaning stated above for polyaspartic acid. The α and β blocks in the above formula can vary in number of repeating units and can be randomly distributed along the chain. The absolute configuration about the asymmetric carbon atom can be D or L.

The molecular weight of the polyglutamates herein can be from about 700 to about 40000, and is preferably in the range of from about 1000 to about 10000, based on the acid form.

Polyglutamic acid can be prepared by known methods, similar to those described for polyaspartic acid.

It is contemplated that a polyamino acid or a water soluble salt thereof consisting of any combination of aspartic acid residues and glutamic acid residues having a molecular weight from about 600 to about 40000, preferably in the range of from about 1000 to about 10000, based on the acid form, is useful in the present invention.

5.3.3. Carboxylated Polysaccharides

The carboxylated polysaccharides used in the method of the present invention have the following formula:

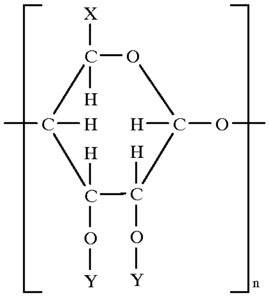

in which X is selected from the free acid or water-soluble salt forms of —COOH, $CH_2OH$, and $CH_2OCH_2COOH$ and Y is selected from —H, and $CH_2COOH$, in which n is a whole integer in a range, the lower limit of which is 10 and the upper limit is determined by the solubility characteristics in an aqueous system; the degree of substitution is 1.0 to 3.0; and the equivalent weight is from 162 to 220, calculated as the acid form. They are derivatives of natural polymers such as carboxylated starches, celluloses, and alginates.

5.3.3. Color Clarification Agents

The cellulase and the polymer may be added either together in a preparation or separately. In a preferred embodiment, the cellulase and polymer is added to an aqueous wash solution. Examples of such wash solutions are disclosed in Section 5.4 (detergent compositions). Cellulase is used in an amount corresponding to about 0.0001–10 mg (calculated as pure enzyme protein) of cellulase per liter of aqueous wash solution (wash liquor) or preferably 0.001–5 mg of cellulase (calculated as pure enzyme protein) per liter of aqueous wash solution, or an amount giving an activity in aqueous washing solution from about 0.001–10,000 CEVU/L, or preferably about 1 to 1000 CEVU/L, and more preferably from about 5–200 CEVU/L. The polymer is used in an amount corresponding to about 0.1–10,000 ppm of the dry weight of the polymer or salt thereof in the aqueous washing solution, preferably about 1–200 ppm, and most preferably about 1–50 ppm. The enzyme and/or polymer preparation may be a water-soluble or water-dispersible solid, liquid, nonaqueous suspension, or water-soluble encapsulated product, particularly a non-dusting granulate or a stabilized liquid. A stabilized liquid is stabilized against microbial infection. Examples of stabilizing agents are inorganic salts, sugars, organic acids, antioxidants.

In one embodiment, fabric is treated with cellulase and polymer during hand washing. In another embodiment, fabric is treated with cellulase and polymer during either commercial or domestic machine washes. A wash cycle is at least about 10 minutes. In one embodiment, a wash cycle is from about 10 minutes to about 90 minutes. In a preferred embodiment, a wash cycle is from about 10 minutes to about 30 minutes. In one embodiment, the cellulase and polymer may be added prior to beginning the wash cycle and/or during the wash cycle. The beneficial effect of adding cellulase plus polymer is increasingly realized with an increasing number of wash cycles. Thus, the value of treatment with cellulase plus polymer is to prolong the acceptable appearance of the fabric, even after many wash cycles. Optimal washing results are obtained when the washing solution is within the range of about pH 6–11, preferably about pH 7–10; when the temperature is in the range of about 5–95° C., preferably about 25–65° C.; and at a liquid to fabric ratio of about 5:1 to 80:1, preferably about 10:1 to 40:1.

5.4 Detergent Compositions

According to the invention, the cellulase and the polymer may typically be components of a detergent composition. The detergent composition of the invention may be in any convenient form, e.g., as powder, granules, paste or liquid. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216. A liquid detergent may be aqueous, typically containing up to 70% water and 0–30% organic solvent, or may be completely nonaqueous.

The detergent composition comprises one or more surfactants, each of which may be anionic, nonionic, cationic, or amphoteric (zwitterionic). The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), alcohol propoxylate, carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as pullulanase, esterase, lipase, cutinase, protease, another cellulase, or peroxidase.

Normally, the detergent contains 1–65% of a detergent builder, or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates as well as layered disilicates and the various types of water-insoluble crystalline or amorphous alumino silicates of which zeolites is the best known representative.

Examples of suitable organic builders include alkali metal, ammonium or substituted ammonium salts of succinates, malonates, fatty acid malonates, fatty acid sulphonates, carboxymethoxy succinates, polyacetates, carboxylates, polycarboxylates, aminopolycarboxylates and polyacetyl carboxylates. The detergent may also be unbuilt, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, polymaleates, maleic/acrylic acid copolymers and lauryl methacrylate/acrylic acid copolymers.

The detergent composition may additionally contain other bleaching agents of the chlorine/bromine-type or the oxygen-type. The bleaching agents may be coated or encapsulated. Examples of inorganic chlorine/bromine-type bleaches are lithium, sodium or calcium hypochlorite or hypobromite as well as chlorinated trisodium phosphate.

Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708. The enzymes of the invention may also be stabilized by adding reversible enzyme inhibitors, e.g., of the protein type as described in EP 0 544 777 B1.

The detergent may also contain other conventional detergent ingredients such as, e.g., fabric conditioners including clays, deflocculant material, foam boosters/foam, suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g. in the range of 7–11.

EXAMPLES

6.1. Example 1

Black cotton fabric and green cotton socks are separately washed in an automatic drum washer at least sixteen times at pH 10 to obtain an accelerated worn appearance that is uniform over the fabric surfaces in each batch. Swatches of uniformly worn black fabric and uniformly worn green socks are added to a standard wash load, and are repeatedly washed at 50° C. using Program No. 1 of an Atlas KT233 Combination Washing/Drying Machine. The Atlas KT233 is a fully automatic drum washer like those described in G.

Jakobi and A. Lohr, "Detergents and Textile Washing," VCH Verlagsgesellschaft mbH (1987) pp.206–208. A commercially available light duty liquid laundry detergent (Soflan®, Colgate-Palmolive) is dosed at a concentration of 5 g/L in tap water during each wash cycle. Washing conditions are as follows:

| Washing Conditions | |
|---|---|
| Apparatus | Atlas KT233 Washing Machine Program No. 1 |
| Wash Volume | 20 L |
| Wash Load | 2.7 kg |
| Wash Liquor | 5 g/L Soflan ® liquid laundry detergent |
| Wash pH | pH 8 |
| Water Hardness | Tap Water (approx. 25 ppm) |
| Wash/Rinse Temperature | 50° C./25° C. |
| Wash/Rinse Time | 30 min./45 min. |
| Dry Temperature | 50° C. |
| Dry Time Between Cycles | 1 hour |
| Number of Cycles | 14 |

Humicola cellulase enzyme (Celluzyme®, Novo Nordisk A/S, U.S. Pat. No. 4,435,307), expressed in Cellulase Viscosity Units per Liter of wash liquor (CEVU/L) and graft polymer of vinyl acetate on polyethylene oxide are dosed in four identical wash experiments as follows:

| Treatment | Humicola cellulase Dose (CEVU/L) | Polyethylene oxide graft polymer (ppm) |
|---|---|---|
| A | 0 | 0 |
| B | 0 | 5 |
| C | 25 | 0 |
| D | 25 | 5 |

After fourteen cycles, black fabric and green socks are separately evaluated for appearance by a panel of five persons. Panelists are instructed to rank the fabrics using reduced pilling (reduced surface fuzz) as the first criterion for choosing the best sample, and using color retention (decreased color loss) as the second criterion for choosing the best sample. Samples are ranked and assigned a number where "4" corresponded to "best," and "1" corresponded to "worst." Scores from five different panelists are averaged to give the following results:

| | Average Panel Score | |
|---|---|---|
| Treatment | Black Fabric | Green Socks |
| A | 1.4 | 1.8 |
| B | 1.6 | 1.2 |
| C | 3 | 3 |
| D | 4 | 4 |

Panelists unanimously rank Treatment D, containing both polymer and cellulase, over Treatment C, containing cellulase only. Treatments C and D are consistently ranked better than Treatments A and B, which did not contain cellulase.

6.2. Example 2

Fabrics from Example 1 are washed another fourteen cycles with increasing doses of Humicola cellulase and polyethylene oxide graft polymer according to the following treatments:

| | Washing Treatments | |
|---|---|---|
| Treatment | Humicola cellulase Dose (CEVU/L) | Polyethylene oxide graft polymer (ppm) |
| A | 0 | 0 |
| B | 0 | 20 |
| C | 100 | 0 |
| D | 100 | 20 |

Fabrics are evaluated by panelists as in Example 1 with the following results:

| | Average Panel Score | |
|---|---|---|
| Treatment | Black Fabric | Green Socks |
| A | 1.2 | 1.2 |
| B | 1.8 | 1.8 |
| C | 3 | 3 |
| D | 4 | 4 |

Again, panelists unanimously rank Treatment D, containing both polymer and cellulase, over Treatment C, containing cellulase only. Treatments C and D are consistently ranked better than Treatments A and B, which did not contain cellulase.

6.3. Example 3

Fabrics from Examples 1 and 2 are evaluated for improved fabric appearance by instrumental methods. Fabric color is evaluated instrumentally using the Macbeth Color Eye and the CIELAB opponent-color coordinate system. In this system, color is described by the values of L*, a*, and b*. Lightness (gray scale) is described by L*, which equals 100 when the measured object is white and decreases to zero when the measured object is black. Red-green is measured by a* (red-positive, green-negative). Yellow-blue is measured by b* (yellow-positive, blue-negative). CIELAB measurements are made after 0, 7, 14, 21, and 28 cycles with the following results:

| | Average a* for Green Socks after Cycle Number | | | | |
|---|---|---|---|---|---|
| Treatment | 0 | 7 | 14 | 21 | 28 |
| A | −12.26 | −10.01 | −8.61 | −6.66 | −6.16 |
| B | −12.38 | −10.38 | −8.85 | −7.80 | −7.91 |
| C | −12.23 | −9.56 | −8.77 | −8.33 | −7.92 |
| D | −12.42 | −11.05 | −11.2 | −10.97 | −10.15 |

A change in a* indicates a change in the original color of the fabric. Treatment D, containing polyethylene oxide graft polymer and cellulase, caused the least change in a* to give the best color retention.

| | Average L* for Black Fabric after Cycle Number | | | | |
|---|---|---|---|---|---|
| Treatment | 0 | 7 | 14 | 21 | 28 |
| A | 29.08 | 31.78 | 32.99 | 34.97 | 36.49 |
| B | 28.96 | 31.54 | 33.62 | 34.76 | 36.30 |
| C | 29.33 | 31.12 | 31.17 | 30.61 | 31.40 |
| D | 29.24 | 30.25 | 29.78 | 29.13 | 29.83 |

An increase in L* for a dark fabric indicates an increase surface grayness. Treatments C and D, containing cellulase, had much lower L*, indicative of better color retention, than Treatments A or B. Treatment D, containing polyethylene oxide graft polymer and cellulase, showed the least amount of graying.

6.4. Example 4

Swatches of uniformly worn black cotton fabric are washed in a Mini-Terg-O-Tometer washing machine. The Mini-Terg-O-Tometer is a small-scale version of the Terg-O-Tometer test washing machine described in Jay. C. Harris, "Detergency Evaluation and Testing," Interscience Publishers Ltd. (1954) pp. 60–61. The following conditions are used:

| | |
|---|---|
| Apparatus | Mini-Terg-O-Tometer |
| Beaker Size | 150 mL |
| Wash Volume | 100 mL |
| Bath Ratio | 1:60 (g:mL) |
| Wash Liquor | Phosphate buffer |
| Wash pH | pH 7.8 |
| Water Hardness | De-ionized |
| Wash/Rinse Temperature | 40° C. |
| Agitation | 150 oscillations/min |
| Time | 30 min. |
| Rinse | 7–15 min in cold tap water |
| Dry | 40 min. hot tumble dry |
| Number of Cycles | 9 |

The wash liquor is 0.05 M Phosphate buffer adjusted to pH 7. Each beaker contained two swatches. Control swatches are dosed with 130 CEVU/L of Humicola cellulase (Celluzyme®, Novo Nordisk A/S, Bagsvaerd, Denmark). Test swatches are dosed with 130 CEVU/L of Celluzyme® and 10 ppm of sodium alginate polymer (SCOTEX XL, Pronova Biopolymer, Inc., Suite 201, 135 Commerce Way, Portsmouth, N.H. 03801).

Panel evaluation of Control and Test swatches is made in a Macbeth SpectraLight II light chamber using the "Cool White" illuminant setting. Panelists are shown the four swatches (two control and two test swatches) and are instructed to rank them in order from best to worst. To obtain an average ranking, the number "4" is assigned to the "best" swatch and the number "1" is assigned to the "worst" swatch. Scores from five different panelists are averaged.

Instrumental evaluation of Control and Test swatch color is made using a Macbeth Color Eye 7000. Measurements are made on the back and front of each swatch. Delta Lx is the average difference in L* between the treated and control swatches. A higher value for Delta Lx corresponds to a "better," darker, less gray appearance. Results from panel score and instrumental evaluation are as follows:

| | Evaluation Method | |
|---|---|---|
| Amt. SCOTEX XL (ppm) | Average Panel Score | Delta Lx |
| 0 | 1.7 | 1.65 |
| 10 | 3.3 | 2.11 |

Panelists and instrumental evaluations agree that test swatches treated with SCOTEX XL have improved color value compared to the control.

6.5. Example 5

Swatches of uniformly worn black cotton fabric are washed in a Mini-Terg-O-Tometer washing machine using the Mini-Terg-O-Tometer Method described in Example 4. The wash liquor is 0.05 M Phosphate buffer adjusted to pH 7. Each beaker contained two swatches. Control swatches are dosed with 130 CEVU/L of Humicola cellulase (Celluzyme®, Novo Nordisk A/S, Bagsvaerd, Denmark). Test swatches are dosed with 130 CEVU/L of Celluzyme® and 10 ppm of a polymer of vinyl acetate grafted on polyethylene oxide (Sokalan HP 22, BASF Corporation, Parsippany, N.J. 07054).

Panel and instrumental evaluations are made as in Example 4. Results appear below:

| | Evaluation Method | |
|---|---|---|
| Amt. Sokalan (ppm) | Average Panel Score | Delta Lx |
| 0 | 1.5 | 1.65 |
| 10 | 3.5 | 2.41 |

Panelists and instrumental evaluations agree that test swatches treated with Sokalan HP 22 have improved color value compared to the control.

6.6. Example 6

Swatches of uniformly worn black cotton fabric are washed in a Mini-Terg-O-Tometer washing machine using the Mini-Terg-O-Tometer Method described in Example 4. The wash liquor is 0.05 M Phosphate buffer adjusted to pH 7. Each beaker contained two swatches. Control swatches are dosed with 130 CEVU/L of Humicola cellulase (Celluzyme®, Novo Nordisk A/S, Bagsvaerd, Denmark). Test swatches are dosed with 130 CEVU/L of Celluzyme® and 10 ppm of the sodium salt of poly-L-aspartic acid (molecular weight 8.5–11.1 kDa, Cat. No. P-5387, SIGMA Chemical Company, P.O. Box 14508 St. Louis, Mo. 63178).

Panel and instrumental evaluations are made as in Example 4. Results appear below:

| | Evaluation Method | |
|---|---|---|
| Amt. Sokalan (ppm) | Average Panel Score | Delta Lx |
| 0 | 1.5 | 1.65 |
| 10 | 3.5 | 2.34 |

Panelists and instrumental evaluations agree that test swatches treated with polyaspartate polymer have improved color value compared to the control.

6.7. Example 7

Swatches of uniformly worn black cotton fabric are washed in a Mini-Terg-O-Tometer washing machine using the Mini-Terg-O-Tometer Method described in Example 4. The wash liquor is 0.05 M Phosphate buffer adjusted to pH 7. Each beaker contained two swatches. Control swatches are dosed with 130 CEVU/L of Humicola cellulase (Celluzyme®, Novo Nordisk A/S, Bagsvaerd, Denmark). Test swatches are dosed with 130 CEVU/L of Celluzyme® and 10 ppm of the sodium salt of poly-L-aspartic acid (molecular weight 8.5–11.1 kDa, Cat. No. P-5387, SIGMA Chemical Company, P.O. Box 14508 St. Louis, Mo. 63178) and 10 ppm of polyethylene glycol (molecular weight 7–9 kDa, P.E.G. 8000, Cat. No. BP233-1, FisherBiotech, Fair Lawn, N.J. 07410).

Panel and instrumental evaluations are made as in Example 4. Results appear below:

| Evaluation Method | | |
|---|---|---|
| Amt. Sokalan (ppm) | Average Panel Score | Delta Lx |
| 0 | 2 | 1.65 |
| 10 | 3 | 2.20 |

Panelists and instrumental evaluations agree that test swatches treated with polyaspartate polymer and polyethylene glycol have improved color value compared to the control.

6.8. Example 8

Swatches of uniformly worn black cotton fabric are washed in a Mini-Terg-O-Tometer washing machine using the Mini-Terg-O-Tometer Method described in Example 4. The wash liquor is 0.05 M Phosphate buffer adjusted to pH 7. Each beaker contained two swatches. Control swatches are dosed with 10 ppm of sodium alginate polymer (SCOTEX XL, Pronova Biopolymer, Inc., Suite 201, 135 Commerce Way, Portsmouth, N.H. 03801). Test swatches are dosed with 10 ppm SCOTEX XL and increasing doses of Humicola cellulase (Celluzyme®, Novo Nordisk A/S, Bagsvaerd, Denmark).

Instrumental evaluation of Control and Test swatch color is made using a Macbeth Color Eye 7000. Measurements are made on the back and front of each swatch. Delta Lx is the average difference in L* between the treated and control swatches. A higher value for Delta Lx corresponds to a "better," darker, less gray appearance. Results appear below:

| Cellulase Dose (CEVU/L) | Delta Lx |
|---|---|
| 0 | −0.76 |
| 30 | 0.72 |
| 130 | 2.11 |

Instrumental evaluations show that test swatches treated with cellulase have improved color value compared to the control.

6.9. Example 9

Swatches of uniformly worn black cotton fabric are washed in a Mini-Terg-O-Tometer washing machine using the Mini-Terg-O-Tometer Method described in Example 4. The wash liquor is 0.05 M Phosphate buffer adjusted to pH 7. Each beaker contained two swatches. Control swatches are dosed with 10 ppm of a polymer of a vinyl acetate grafted on polyethylene oxide (Sokalan HP 22, BASF Corporation, Parsippany, N.J.). Test swatches are dosed with 10 ppm Sokalan HP 22 and increasing doses of Humicola cellulase (Celluzyme®, Novo Nordisk A/S, Bagsvaerd, Denmark).

Instrumental evaluation of Control and Test swatch color is made as described in Example 8. Results appear below:

| Cellulase Dose (CEVU/L) | Delta Lx |
|---|---|
| 0 | −0.30 |
| 30 | 1.20 |
| 130 | 2.41 |

Instrumental evaluations show that test swatches treated with cellulase have improved color value compared to the control.

6.10. Example 10

Swatches of uniformly worn black cotton fabric are washed in a Mini-Terg-O-Tometer washing machine using the Mini-Terg-O-Tometer Method described in Example 4. The wash liquor is 0.05 M Phosphate buffer adjusted to pH 7. Each beaker contained two swatches. Control swatches are dosed with 10 ppm of the sodium salt of poly-L-aspartic acid (molecular weight 8.5–11.1 kDa, Cat. No. P-5387, SIGMA Chemical Company, P.O. Box 14508 St. Louis, Mo. 63178). Test swatches are dosed with 10 ppm of poly-L-aspartic acid and increasing doses of Humicola cellulase (Celluzyme®, Novo Nordisk A/S, Bagsvaerd, Denmark).

Instrumental evaluation of Control and Test swatch color is made as described in Example 8. Results appear below:

| Cellulase Dose (CEVU/L) | Delta Lx |
|---|---|
| 0 | −0.55 |
| 30 | 1.18 |
| 130 | 2.34 |

Instrumental evaluations show that test swatches treated with cellulase have improved color value compared to the control.

6.11. Example 11

Swatches of uniformly worn black cotton fabric are washed in a Mini-Terg-O-Tometer washing machine using the Mini-Terg-O-Tometer Method described in Example 4. The wash liquor is 0.05 M Phosphate buffer adjusted to pH 7. Each beaker contained two swatches. Control swatches are dosed with 10 ppm of the sodium salt of poly-L-aspartic acid (molecular weight 8.5–11.1 kDa, Cat. No. P-5387, SIGMA Chemical Company, P.O. Box 14508 St. Louis, Mo. 63178) and 10 ppm of polyethylene glycol (molecular weight 7–9 kDa, P.E.G. 8000, Cat. No. BP233-1, FisherBiotech, Fair Lawn, N.J. 07410). Test swatches are dosed with 10 ppm of poly-L-aspartic acid, 10 ppm P.E.G. 8000, and increasing doses of Humicola cellulase (Celluzyme®, Novo Nordisk A/S, Bagsvaerd, Denmark).

Instrumental evaluation of Control and Test swatch color is made as described in Example 8. Results appear below:

| Cellulase Dose (CEVU/L) | Delta Lx |
|---|---|
| 0 | −0.65 |
| 30 | 1.38 |
| 130 | 2.20 |

Instrumental evaluations show that test swatches treated with cellulase have improved color value compared to the control.

6.12. Example 12

Swatches of uniformly worn black cotton fabric are washed in a Mini-Terg-O-Tometer washing machine using the Mini-Terg-O-Tometer method described in Example 4. The wash liquor is 2 g/L of a commercial light duty liquid laundry detergent (Soflan®, Colgate-Palmolive). The wash pH is 8–9. Test swatches are dosed with a sodium alginate polymer (SCOTEX XL® from Pronova Biopolymer, Inc., Suite 201, 135 Commerce Way, Portsmouth, N.H. 03801). SCOTEX XL is an example of a carboxylated polysaccharide. SCOTEX XL is a naturally occurring linear alginate copolymer, recovered from seaweeds, comprised in the sodium salt form of β-D-mannuronic acid and α-L-guluronic acid units linked by (1->4) glycosidic bonds. Treated and control swatches are evaluated in pairs by six panelists. Panelists are instructed to select the "best" swatch in each pair. To obtain an average ranking, the number "2" is assigned to swatches ranked "best" and the number "1" is assigned to swatches ranked "worse." Scores are averaged. The results are as follows:

| Test Set | Enzyme Dose (CEVU/L) | SCOTEX Dose (ppm) | Average Panel Score |
|---|---|---|---|
| A | 0 | 0 | 1.0 |
| | 0 | 5 | 2.0 |
| B | 0 | 0 | 1.0 |
| | 0 | 10 | 2.0 |
| C | 33 | 0 | 1.0 |
| | 26 | 5 | 2.0 |
| D | 66 | 0 | 1.0 |
| | 53 | 5 | 2.0 |
| E | 66 | 0 | 1.0 |
| | 53 | 10 | 2.0 |

In each case, swatches treated with sodium alginate are ranked as better than swatches treated without sodium alginate, even though SCOTEX treated swatches are dosed with slightly lower amounts of cellulase.

The panel results are consistent with instrumental color evaluations of treated swatches, expressed as Delta Lx. Increasing Delta Lx corresponds to a "better," darker, less gray appearance.

| | Delta Lx | |
|---|---|---|
| Cellulase Dose (CEVU/L) | 5 ppm | 10 ppm |
| 0 | 0.03 | 0.39 |
| 26 | 1.36 | 1.46 |
| 53 | 1.22 | 2.00 |

Further results are shown in FIG. 1. It appears that SCOTEX XL gives significantly increased color clarification performance in the European-type liquid laundry detergent. SCOTEX XL also appears to boost the action of cellulase.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A color clarification method comprising treating a colored fabric with a cellulase and a polymer selected from the group consisting of a polyalkylene oxide graft polymer, a polyamino acid polymer, and a carboxylated polysaccharide polymer in an amount effective to preserve the color of the fabric relative to a fabric treated without polymer but with cellulase or without cellulase but with polymer after at least one wash cycle, in which said polymer is present in an amount of about 1–200 ppm of dry weight of the polymer in an aqueous washing solution.

2. The method according to claim 1 in which the colored fabric is treated with a fungal cellulase.

3. The method according to claim 2 in which the fungal cellulase is a Humicola cellulase.

4. The method according to claim 1 in which the colored fabric is treated with a bacterial cellulase.

5. The method according to claim 1 in which the colored fabric is treated with at least one multicomponent cellulase.

6. The method according to claim 1 in which the colored fabric is treated with at least one monocomponent cellulase.

7. The method according to claim 1 in which the colored fabric is treated with a multicomponent cellulase and a monocomponent cellulase.

8. The method according to claim 1 in which the polymer is a polyamino acid polymer.

9. The method according to claim 1 in which the polymer is a polyaspartic acid polymer.

10. The method according to claim 1 in which the polymer is a polyglutamic acid polymer.

11. The method according to claim 1 in which the polymer is a sodium alginate polymer.

12. The method according to claim 1 in which the polymer is a polyethylene oxide graft polymer.

13. The method according to claim 1 in which the polymer is a polyethylene oxide polymer grafted with monomers of C2–C6 vinyl esters.

14. The method according to claim 1 in which the fabric is treated with said cellulase and said polymer for about 10 to about 90 minutes.

15. The method according to claim 1 in which the fabric is treated with said cellulase and said polymer for about 10 to about 30 minutes.

16. The method according to claim 1 in which the fabric is treated with said cellulase and said polymer at about 5–95° C.

17. The method according to claim 1 in which the fabric is treated with said cellulase and said polymer at about 25–65° C.

18. The method according to claim 1 in which the fabric is treated with said cellulase and said polymer at a pH of about 6–11.

19. The method according to claim 1 in which the fabric is treated with said cellulase and said polymer at a pH of about 7–10.

20. The method according to claim 1 in which the polymer is present in an amount of about 1–50 ppm of dry weight of the polymer in the aqueous washing solution.

* * * * *